(12) United States Patent
Harada (10) Patent No.: US 9,717,469 B2
(45) Date of Patent: Aug. 1, 2017

(54) X-RAY COMPUTED TOMOGRAPHY APPARATUS, HIGH VOLTAGE GENERATION DEVICE, AND RADIOLOGICAL IMAGE DIAGNOSTIC APPARATUS

(71) Applicant: Toshiba Medical Systems Corporation, Otawara-shi (JP)

(72) Inventor: Sanae Harada, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 486 days.

(21) Appl. No.: 14/458,690

(22) Filed: Aug. 13, 2014

(65) Prior Publication Data

US 2014/0355736 A1    Dec. 4, 2014

Related U.S. Application Data

(63) Continuation of application No. PCT/JP2013/073452, filed on Aug. 30, 2013.

(30) Foreign Application Priority Data

Aug. 31, 2012 (JP) ................................. 2012-191621
Aug. 30, 2013 (JP) ................................. 2013-180471

(51) Int. Cl.
*H05G 1/32* (2006.01)
*H05G 1/36* (2006.01)
(Continued)

(52) U.S. Cl.
CPC .................. *A61B 6/56* (2013.01); *A61B 6/03* (2013.01); *A61B 6/40* (2013.01); *H01J 35/26* (2013.01);
(Continued)

(58) Field of Classification Search
CPC .... A61B 6/03; A61B 6/56; A61B 6/40; A61B 6/4441; H05G 1/32; H05G 1/46; H05G 1/36; H05G 1/62; H01J 35/26
See application file for complete search history.

(56) References Cited

U.S. PATENT DOCUMENTS

| | | | |
|---|---|---|---|
| 4,819,259 A * | 4/1989 | Tanaka ..................... | H05G 1/36 318/806 |
| 5,313,510 A | 5/1994 | Ebersberger et al. | |

(Continued)

FOREIGN PATENT DOCUMENTS

JP    3-156844 A    7/1991
JP    05-217534 A   8/1993
(Continued)

OTHER PUBLICATIONS

Translation of JP 2010-063758, published on Mar. 25, 2010.*
(Continued)

*Primary Examiner* — Glen Kao
*Assistant Examiner* — Chih-Cheng Kao
(74) *Attorney, Agent, or Firm* — Oblon, McClelland, Maier & Neustadt, L.L.P.

(57) ABSTRACT

According to one embodiment, Switching units are configured to switch the intensity of X-rays to be generated by an anode. An X-ray controller controls the switching units to switch the intensity of the X-rays to be generated by the anode, and controls a rotor control power generator to rotate the anode. When a value approximately equal to an integer multiple of an X-ray intensity switching period designated by a user coincides with the rotor rotation period, the X-ray controller controls the rotor control power generator to shift the thermoelectron collision ranges of the anode in the first turn from thermoelectron collision ranges in the second turn.

13 Claims, 8 Drawing Sheets

(51) Int. Cl.
  *H05G 1/46* (2006.01)
  *H01J 35/26* (2006.01)
  *A61B 6/00* (2006.01)
  *A61B 6/03* (2006.01)
  *H05G 1/62* (2006.01)

(52) U.S. Cl.
  CPC ............... *H05G 1/32* (2013.01); *H05G 1/36* (2013.01); *H05G 1/46* (2013.01); *H05G 1/62* (2013.01); *A61B 6/4441* (2013.01)

(56) References Cited

U.S. PATENT DOCUMENTS

| | | | |
|---|---|---|---|
| 7,496,180 | B1 | 2/2009 | Subraya et al. |
| 2004/0109537 | A1* | 6/2004 | Nakamura ............... H05G 1/10 378/111 |
| 2005/0084073 | A1* | 4/2005 | Seppi ..................... A61B 6/032 378/156 |
| 2009/0154649 | A1 | 6/2009 | Behling |
| 2010/0183117 | A1 | 7/2010 | Tsumuraya et al. |
| 2010/0215141 | A1* | 8/2010 | Kondo ................... A61B 6/032 378/16 |

FOREIGN PATENT DOCUMENTS

| | | |
|---|---|---|
| JP | 2009-059695 A | 3/2009 |
| JP | 2009-538500 A | 11/2009 |
| JP | 2010-063758 A | 3/2010 |
| JP | 2010-148920 A | 7/2010 |
| JP | 2011-200532 A | 10/2011 |
| JP | 2012-235935 A | 12/2012 |
| WO | WO 2009/011422 A1 | 1/2009 |

OTHER PUBLICATIONS

International Search Report mailed Oct. 1, 2013 for PCT/JP2013/073452 filed Aug. 30, 2013 (with partial English Translation).
International Written Opinion mailed Oct. 1, 2013 for PCT/JP2013/073452 filed Aug. 30, 2013.

* cited by examiner

X-ray modulation control

Rotor rotation period: 10 msec (100 Hz)
X-ray intensity switching period: 1 msec (1 kHz)

■ : High-current thermoelectron collision plane (X-ray HIGH)
☐ : Low-current thermoelectron collision plane (X-ray LOW)

(a) Anode (b) X-ray emission sequence

X-RAY COMPUTED TOMOGRAPHY APPARATUS, HIGH VOLTAGE GENERATION DEVICE, AND RADIOLOGICAL IMAGE DIAGNOSTIC APPARATUS

CROSS-REFERENCE TO RELATED APPLICATIONS

This application is a Continuation Application of PCT Application No. PCT/JP2013/073452, filed Aug. 30, 2013 and based upon and claims the benefit of priority from the Japanese Patent Application No. 2012-191621, filed Aug. 31, 2012, and No. 2013-180471, filed Aug. 30, 2013, the entire contents of all of which are incorporated herein by reference.

FIELD

Embodiments described herein relate generally to an X-ray computed tomography apparatus, high voltage generation device, and radiological image diagnostic apparatus.

BACKGROUND

X-ray computed tomography apparatuses require high-speed X-ray ON/OFF control and high-speed X-ray modulation. The high-speed X-ray ON/OFF control and high-speed X-ray modulation can be realized by controlling a bias voltage to be applied to a bias electrode in an X-ray tube.

An anode in the X-ray tube rotates typically at a rotational frequency of about 50 to 200 Hz, that is, in a rotation period of about 5 to 20 msec. When high-speed X-ray ON/OFF control or high-speed X-ray modulation is executed in this rotation period, the X-ray intensity is switched several to several ten times while the anode rotates once. For example, when a multiple of the X-ray ON/OFF switching period coincides with the rotation period of the anode, electron beams bombard only limited portions of the anode. Temperature nonuniformity is therefore generated on the anode, and there is a fear of local partial damage to the anode at only the limited portions. The partial damage causes anode roughening and may cause discharge or nonuniformity of the X-ray dose.

It is an object of embodiments to provide an X-ray computed tomography apparatus, high voltage generation device, and radiological image diagnostic apparatus capable of reducing partial damage to the anode.

DETAILED DESCRIPTION

In general, according to one embodiment, an X-ray computed tomography apparatus includes an X-ray tube device, an X-ray detector, a rotating unit, a power supply unit, a switching unit, a control unit. The X-ray tube device includes a cathode configured to generate a thermoelectron, an anode configured to generate an X-ray upon receiving the thermoelectron generated by the cathode, and a support mechanism configured to support the anode to be rotatable about a rotation axis. The X-ray detector is configured to detect the X-ray generated by the X-ray tube device. The rotating unit is configured to support the X-ray tube device to be rotatable about a subject. The power supply unit is configured to supply power to the support mechanism. The switching unit is configured to switch an intensity of an X-ray to be generated by the anode. The control unit is configured to control the switching unit to switch the intensity of the X-ray to be generated by the anode, and control the power supply unit to rotate the anode, when a value substantially equal to an integer multiple of a switching period of the intensity of the X-ray coincides with a rotation period of the anode, the control unit controlling the power supply unit to shift at least some thermoelectron collision ranges of the anode in a first turn from thermoelectron collision ranges in a second turn.

An X-ray computed tomography apparatus, high voltage generation device, and radiological image diagnostic apparatus according to an embodiment will now be described with reference to the accompanying drawings.

The radiological image diagnostic apparatus according to the embodiment is a general term of image diagnostic apparatuses that use radiation such as an X-ray. Examples of the radiological image diagnostic apparatus according to the embodiment are an X-ray computed tomography apparatus and X-ray diagnostic apparatus which generate X-rays upon receiving application of a high voltage from a high voltage generation device.

Figure 1:
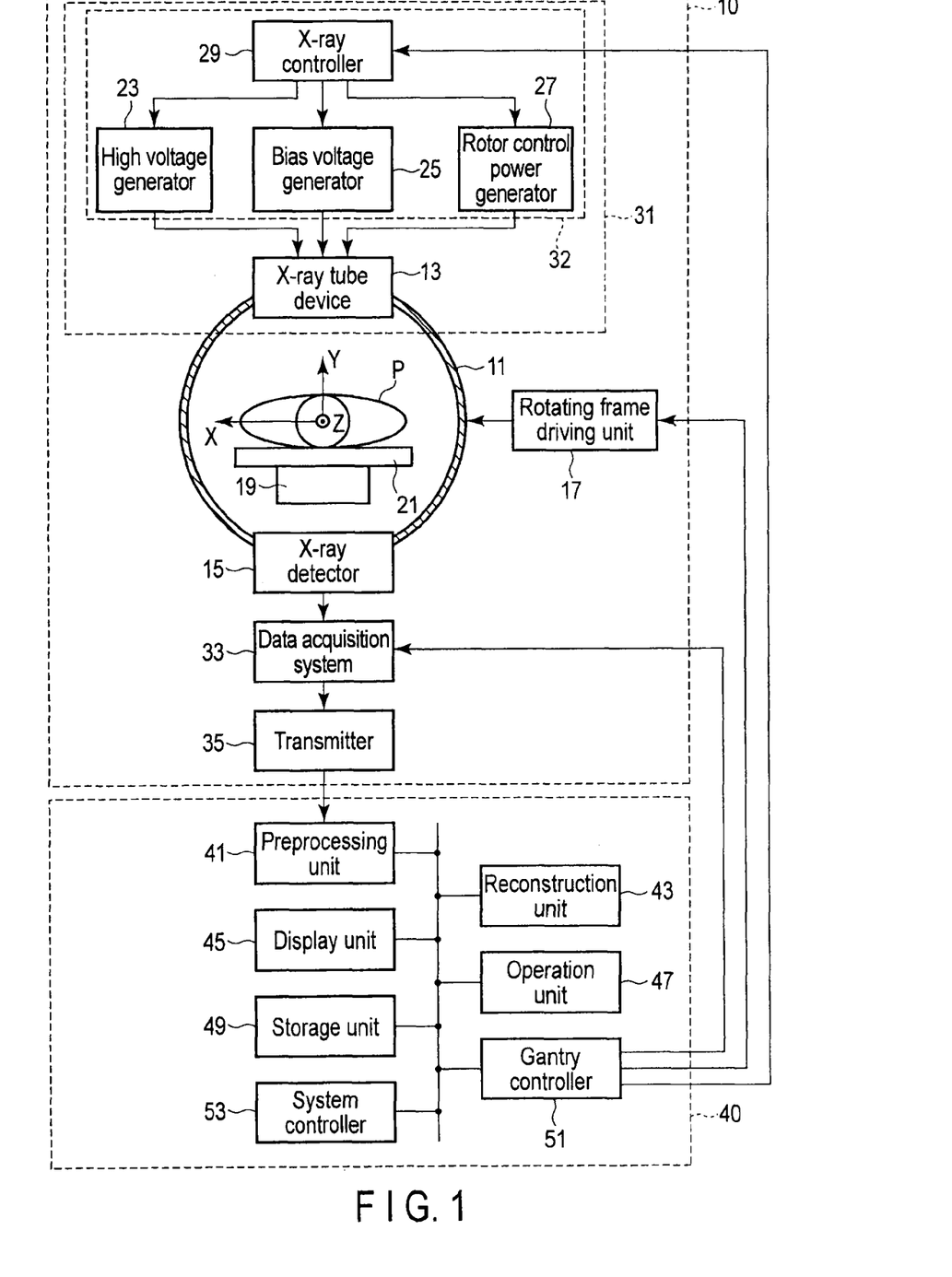
FIG. 1 is a view showing the arrangement of an X-ray computed tomography apparatus according to an embodiment.

FIG. 1 is a view showing the arrangement of an X-ray computed tomography apparatus according to the embodiment. As shown in FIG. 1, an X-ray computed tomography apparatus 1 includes a gantry 10 and console 40, as shown in FIG. 1.

The gantry 10 includes an annular or disc-like rotating frame 11. The rotating frame 11 supports an X-ray tube device 13 and X-ray detector 15 to be rotatable about the center axis (rotation axis) of the rotating frame 11. An FOV (Field Of View) is set in the opening of the rotating frame 11. The rotating frame 11 is connected to a rotating frame driving unit 17. The rotating frame driving unit 17 rotates the rotating frame 11 at a predetermined angular velocity according to control by a gantry controller 51 in the console 40 to rotate the X-ray tube device 13 and X-ray detector 15 about the rotation axis.

Note that the Z-axis is defined along the rotation axis of the rotating frame 11. The Y-axis is defined along an axis connecting the X-ray focus of the X-ray tube device 13 and the center of the detection surface of the X-ray detector 15. The Y-axis is perpendicular to the Z-axis. The X-axis is defined along an axis perpendicular to the Y- and Z-axes. The XYZ orthogonal coordinate system constitutes a rotating coordinate system which rotates upon rotation of the rotating frame 11.

A top support mechanism 19 is installed near the rotating frame 11. The top support mechanism 19 supports a top 21 to be movable along the Z-axis. The top support mechanism 19 supports the top 21 so that the major axis of the top 21 becomes parallel to the Z-axis. A subject P is placed on the top 21. The top support mechanism 19 is equipped with a motor (not shown). By power generated by the motor, the top support mechanism 19 moves the top 21 along the Z-axis.

The X-ray tube device 13 is connected to a high voltage generator 23, bias voltage generator 25, and rotor control power generator 27. The high voltage generator 23, bias voltage generator 25, and rotor control power generator 27 are connected to an X-ray controller 29. The X-ray tube device 13, high voltage generator 23, bias voltage generator 25, rotor control power generator 27, and X-ray controller 29 constitute an X-ray generation device 31. Also, the high voltage generator 23, bias voltage generator 25, rotor control power generator 27, and X-ray controller 29 constitute a high voltage generation device 32. The high voltage generation device 32 is connected to the X-ray tube device 13. In other words, the X-ray generation device 31 includes the X-ray tube device 13 and high voltage generation device 32. The X-ray generation device 31 generates X-rays from an X-ray tube while alternately switching the X-ray intensity between a low intensity and a high intensity in accordance with control by the gantry controller 51. Here, an X-ray emission control method of alternately repeating a low intensity of zero and a high intensity of non-zero, that is, emission and cutoff of X-rays will be called X-ray ON/OFF control. Control in which both low and high intensities are non-zero will be called X-ray modulation control. The X-ray intensity is defined by a tube voltage value and tube current value. Details of the X-ray generation device 31 will be described later.

The X-ray detector 15 detects X-rays generated by the X-ray tube device 13. The X-ray detector 15 includes a plurality of detection elements arrayed two-dimensionally. For example, the plurality of detection elements are arrayed along an arc centered on the rotation axis Z of the rotating frame 11. The detection element array direction along the arc is called a channel direction. A plurality of detection elements arrayed in the channel direction are called a detection element row. A plurality of rows of detection elements are arrayed in the column direction along the rotation axis Z. Each detection element detects X-rays generated by the X-ray tube device 13, and generates an electrical signal (current signal) corresponding to the intensity of the detected X-rays. The generated electrical signal is supplied to a data acquisition system (DAS) 33.

The data acquisition system 33 acquires electrical signals for respective views via the X-ray detector 15 according to control by the gantry controller 51. As is well known, a view corresponds to a rotation angle of the rotating frame 11 about the rotation axis Z. In terms of signal processing, a view corresponds to a sampling point of data during rotation of the rotating frame 11. The data acquisition system 33 converts the acquired analog electrical signal into digital data. The digital data is called raw data. A non-contact transmitter 35 supplies the raw data to the console 40 for each predetermined view.

The console 40 includes a preprocessing unit 41, a reconstruction unit 43, a display unit 45, an operation unit 47, a storage unit 49, the gantry controller 51, and a system controller 53.

The preprocessing unit 41 performs preprocessing including logarithmic transformation and sensitivity correction for the raw data supplied from the data acquisition system 33. The preprocessed data is called projection data. Based on the projection data, the reconstruction unit 43 reconstructs image data concerning a subject. The display unit 45 displays the image data generated by the reconstruction unit 43 on a display device. The operation unit 47 accepts various instructions and information inputs from a user via an input device. The storage unit 49 stores the raw data, projection data, and image data. The storage unit 49 also stores a control program. The gantry controller 51 controls the rotating frame driving unit 17, X-ray generation device 31, and data acquisition system 33 in order to execute X-ray CT tomography. The system controller 53 reads out the control program stored in the storage unit 49, expands it in a memory, and controls the respective units in accordance with the expanded control program.

Figure 2:
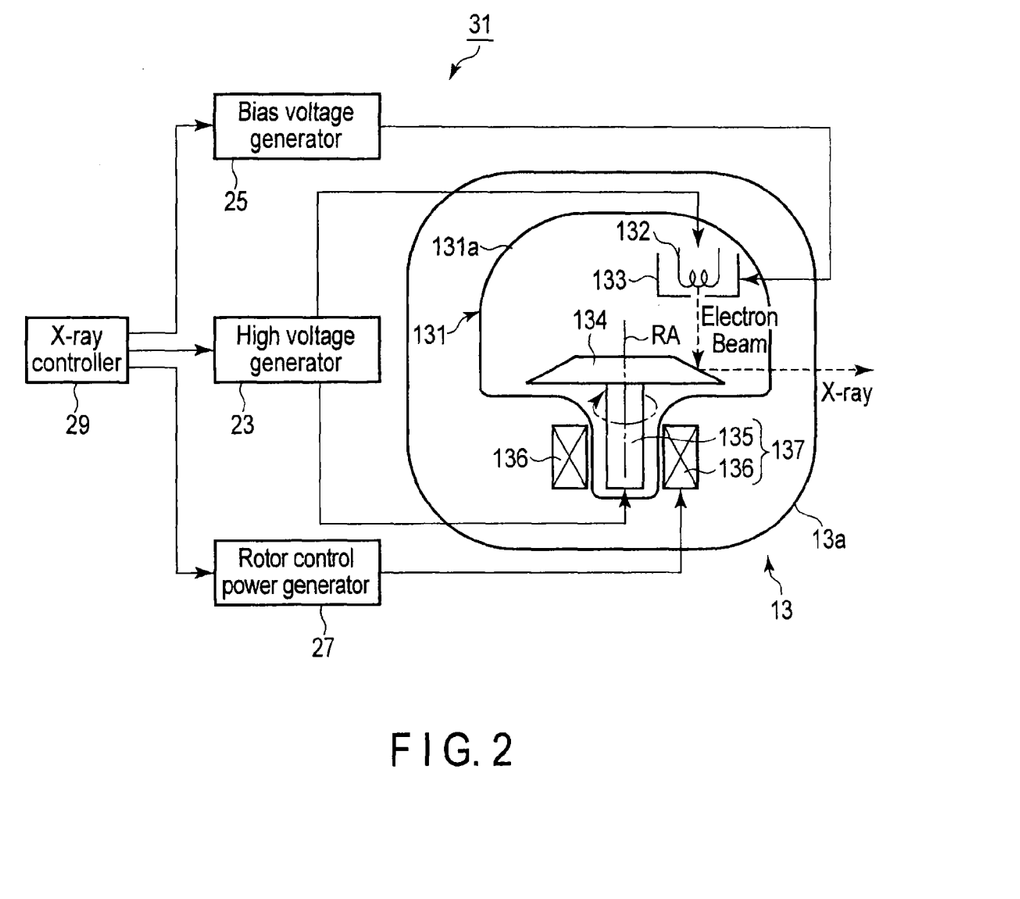
FIG. 2 is a view schematically showing the arrangement of an X-ray generation device in FIG. 1.

Next, the arrangement of the X-ray generation device 31 will be explained in detail with reference to FIG. 2. FIG. 2 is a view schematically showing the arrangement of the X-ray generation device 31. As shown in FIG. 2, the X-ray generation device 31 includes the X-ray controller 29 serving as a control center, the X-ray tube device 13, the high voltage generator 23, the bias voltage generator 25, and the rotor control power generator 27. The X-ray tube device 13 is equipped with an X-ray tube container 13a. The X-ray tube container 13a accommodates an X-ray tube 131. The space between the X-ray tube container 13a and the X-ray tube 131 is filled with an insulating oil.

The X-ray tube 131 is equipped with a housing 131a. The inside of the housing 131a is kept in vacuum. The housing 131a is made of a material such as glass or metal. The housing 131a incorporates a cathode 132, bias electrode 133, anode 134, and rotator (to be referred to as a rotor hereinafter) 135. The cathode 132 includes a filament. The cathode 132 is connected to the high voltage generator 23 via a cable or the like. The high voltage generator 23 supplies a filament current to the cathode 132. Upon receiving the supply of the filament current, the cathode 132 generates heat and emits thermoelectrons. The anode 134 is a disc-shaped electrode formed from a heavy metal such as tungsten or molybdenum. The rotor 135 is attached to the anode 134. The rotor 135 is arranged along a rotation axis RA of the anode 134. A stationary part (to be referred to as a stator hereinafter) 136 is attached outside the housing 131a to surround the rotor 135. The stator 136 is accommodated in the X-ray tube container 13a. The stator 136 and rotor 135 constitute a support mechanism 137 which supports the anode 134 to be rotatable about the rotation axis RA. The support mechanism 137, more specifically, the stator 136 is connected to the rotor control power generator 27. The rotor control power generator 27 supplies, to the stator 136, power for rotating the rotor 135 about the rotation axis RA. Upon receiving the supply of the power, the stator 136 rotates the rotor 135 on the basis of the electromagnetic induction principle. Along with the rotation of the rotor 135, the anode 134 rotates. The anode 134 and high voltage generator 23 are connected via the rotor 135. The high voltage generator 23 applies a high voltage between the cathode 132 and the anode 134. Thermoelectrons generated by the cathode 132 are accelerated by the high voltage applied between the cathode 132 and the anode 134 while converging into a beam, and collide with the anode 134 during rotation. Upon being bombarded with the thermoelectrons from the cathode 132, the anode 134 emits X-rays toward an X-ray irradiation window formed in the X-ray tube container 13a. The bias electrode 133 is interposed between the cathode 132 and the anode 134. The bias electrode 133 is connected to the bias voltage generator 25. The bias voltage generator 25 applies a bias voltage to the bias electrode 133 to block the thermoelectrons emitted by the cathode 132. The number of thermoelectrons colliding with the anode 134 is changed by adjusting a potential with respect to the cathode potential based on the bias voltage.

As described above, the X-ray controller 29 controls the high voltage generator 23, bias voltage generator 25, and rotor control power generator 27 in accordance with control from the gantry controller 51.

More specifically, the X-ray controller 29 controls the high voltage generator 23 in accordance with a preset tube voltage value and tube current value in X-ray CT tomography, and controls the X-ray tube device 13 to generate X-rays of an intensity corresponding to the tube voltage value and tube current value.

In X-ray CT tomography, the X-ray controller 29 controls the rotor control power generator 27 to rotate the rotor 135 in accordance with the set value of the rotation period of the rotor 135 (to be referred to as a rotor rotation period hereinafter). The rotor control power generator 27 supplies power to the stator 136 to rotate the rotor 135 in a rotor rotation period corresponding to this set value. The rotor rotation period is typically set to an arbitrary value of about 5 to 20 msec (i.e., a rotational speed of 50 to 200 Hz).

In X-ray CT tomography, the X-ray controller 29 executes X-ray intensity switching by an X-ray generation method selected in accordance with an instruction from the user via the operation unit 47 in synchronism with the data acquisition period of the data acquisition system 33. As described above, the X-ray generation method is appropriately selected from X-ray ON/OFF control and X-ray modulation control. In X-ray ON/OFF control, the X-ray controller 29 controls the bias voltage generator 25 to alternately switch cutoff and emission of X-rays in a predetermined switching period. When cutting off X-rays, the bias voltage generator 25 switches the bias voltage to a relatively large value so that the tube current becomes zero. In emission of X-rays, the bias voltage generator 25 switches the bias voltage to zero so that the tube current flows.

X-ray modulation control includes two types: tube current modulation control and tube voltage modulation control. In the embodiment, either of these two methods can be executed. For descriptive convenience, X-ray modulation control is assumed to be tube current modulation control. In tube current modulation control, the X-ray controller 29 controls the bias voltage generator 25 to alternately switch between the first tube current value and the second tube current value in accordance with a predetermined X-ray intensity switching period. The bias voltage generator 25 alternately applies, to the bias electrode 133, a bias voltage corresponding to the first tube current value and a bias voltage corresponding to the second tube current value in accordance with the X-ray intensity switching period. The X-ray intensity switching period in the embodiment is set to a high order of about 1 kHz to 4 kHz, compared to a conventional switching period of several Hz to several ten Hz. That is, the X-ray intensity is switched several times while the anode 134 rotates once.

Typically, a user designates the X-ray intensity switching period and rotor rotation period. When a multiple of the X-ray intensity switching period coincides with the rotor rotation period, thermoelectrons collide with only local portions of the anode 134 on the electron beam orbital plane, and partial damage to the anode may take place.

Figure 3:
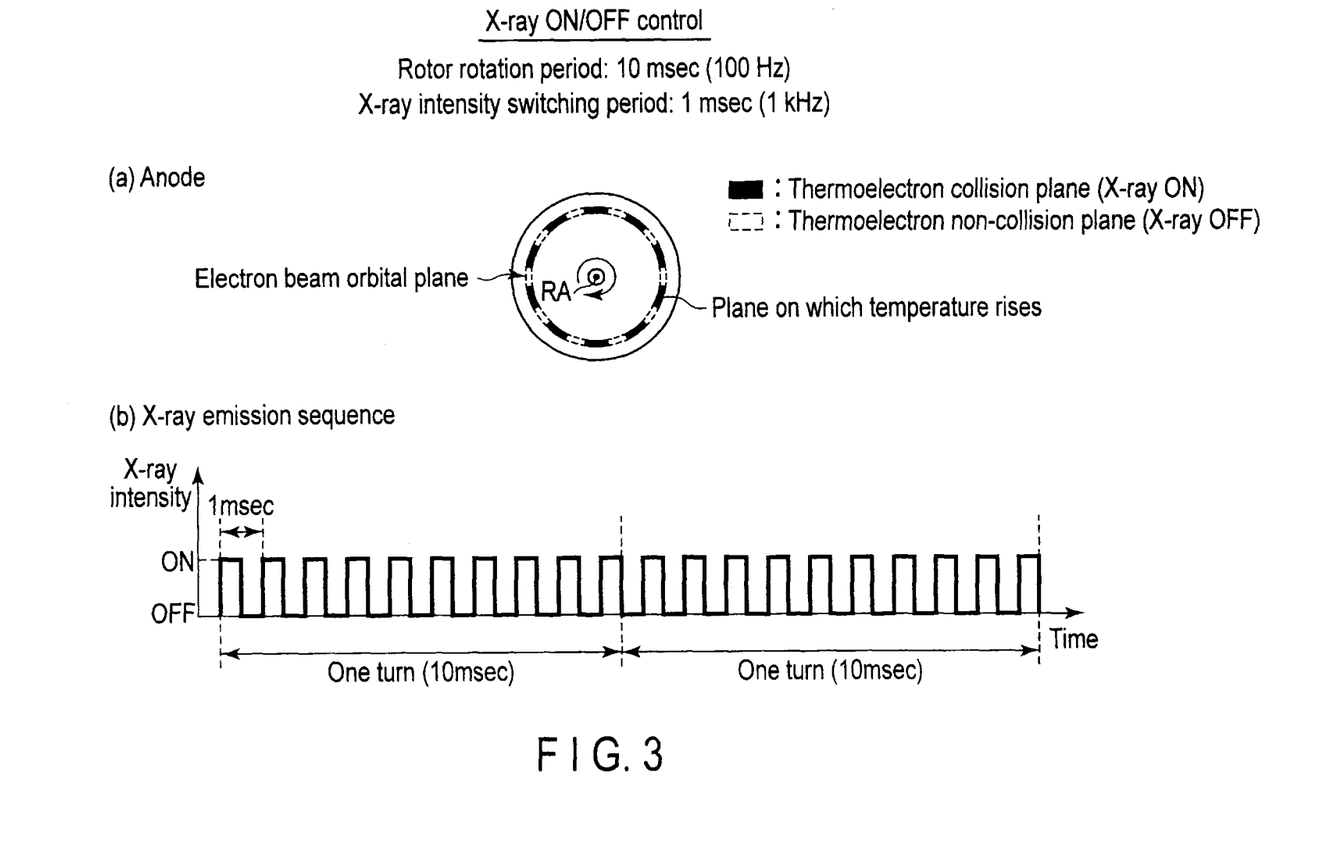
FIG. 3 is a view for explaining partial damage to an anode in X-ray ON/OFF control by an X-ray controller in FIG. 2.

FIG. 3 is a view for explaining partial damage to the anode 134 in X-ray ON/OFF control. In FIG. 3, (a) is a schematic view of the anode 134 when viewed from the cathode 132. In FIG. 3, (b) shows an X-ray emission sequence by the X-ray controller 29. In FIG. 3, assume that the rotor rotation period is 10 msec (100 Hz), and the X-ray intensity switching period is 1 msec (1 kHz). Since a decuple of the X-ray intensity switching period coincides with the rotor rotation period, X-ray ON/OFF switching is regularly repeated 10 times in every turn of the rotor, as shown in (b) of FIG. 3. In this case, as shown in (a) of FIG. 3, even when the anode 134 rotates a plurality of turns, thermoelectrons collide with only the same local portions on the electron beam orbital plane. In this manner, when an integer multiple of the X-ray intensity switching period coincides with the rotor rotation period, thermoelectrons do not uniformly collide on the electron beam orbital plane, but collide with only local portions. Here, a portion with which thermoelectrons actually collide on the anode 134 will be called an electron collision surface, and a portion with which no thermoelectron collides will be called a thermoelectron non-collision surface. When an integer multiple of the X-ray intensity switching period coincides with the rotor rotation period, damage to the anode 134 arising from electron collision greatly differs between the electron collision surface and the electron non-collision surface on the electron beam orbital plane.

Figure 4:
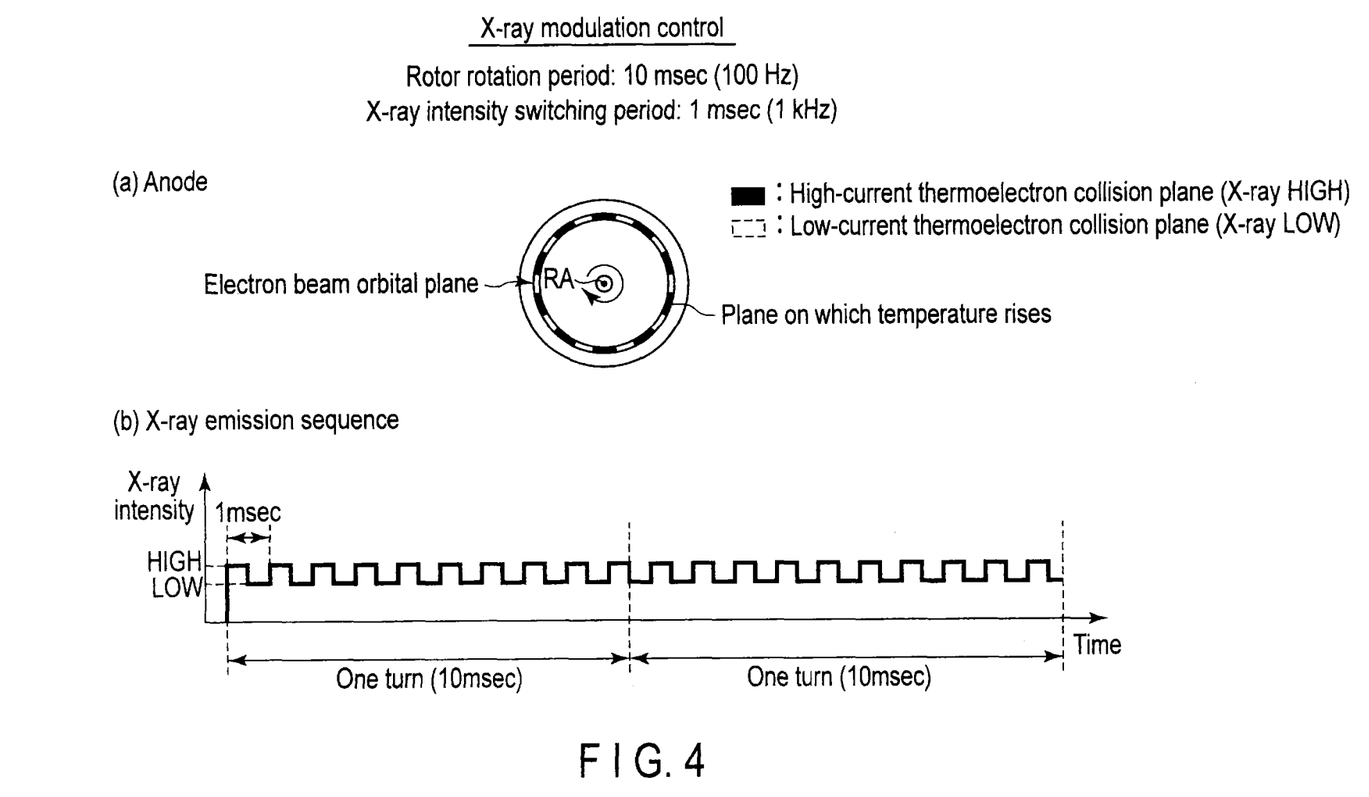
FIG. 4 is a view for explaining partial damage to the anode in X-ray modulation control by the X-ray controller in FIG. 2.

FIG. 4 is a view for explaining partial damage to the anode 134 in X-ray modulation control. In FIG. 4, (a) is a schematic view of the anode when viewed from the cathode 132. In FIG. 4, (b) shows an X-ray emission sequence by the X-ray controller 29. In FIG. 4, similar to FIG. 3, assume that the rotor rotation period is 10 msec (100 Hz), and the X-ray intensity switching period is 1 msec (1 kHz). As shown in (b) of FIG. 4, switching of the X-ray intensity between HIGH and LOW is periodically repeated 10 times in every turn of the rotor. The cathode 132 emits thermoelectrons of a high current in the HIGH period of the X-ray intensity, and emits thermoelectrons of a low current in the LOW period of the X-ray intensity. In X-ray modulation control, when a decuple of the X-ray intensity switching period coincides with the rotor rotation period, thermoelectrons of a high current periodically collide with the same local portions on the electron beam orbital plane over a plurality of turns. Even in X-ray modulation control, as well as X-ray ON/OFF control, when an integer multiple of the X-ray intensity switching period coincides with the rotor rotation period, damage to the anode 134 becomes greatly different on the electron beam orbital plane.

Considering this, when a multiple of the X-ray intensity switching period coincides with the rotor rotation period, the X-ray controller 29 according to the embodiment changes the rotor rotation period so that damage to the anode 134 by thermoelectron collision is uniformly distributed on the electron beam orbital plane. An example of the operation of rotation period change processing to be performed by the X-ray controller 29 will be explained. In the following operation example, the X-ray generation method is assumed to be X-ray ON/OFF control for descriptive convenience.

Figure 5:
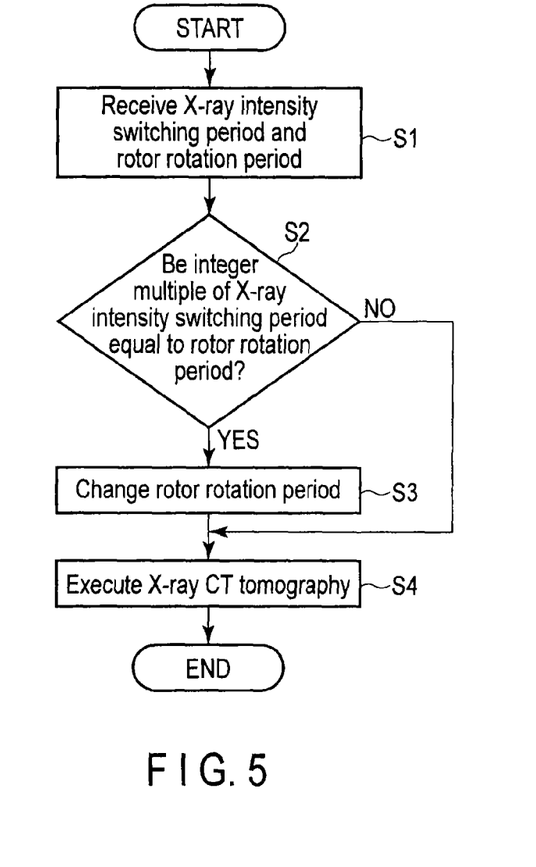
FIG. 5 is a flowchart showing a typical sequence of rotation period change processing to be performed by the X-ray controller in FIG. 2.

FIG. 5 is a flowchart showing a typical sequence of rotation period change processing to be performed by the X-ray controller 29. As shown in FIG. 5, first, the X-ray controller 29 receives an initially set X-ray intensity switching period and rotor rotation period from the console 40 (step S1). The X-ray intensity switching period and rotor rotation period are set by, e.g., the system controller 53 in accordance with an instruction from the user via the operation unit 47 before X-ray emission. Data of the X-ray intensity switching period and rotor rotation period are transmitted from the console 40 to the gantry 10. In addition, the console 40 transmits, to the gantry 10, data of other imaging conditions such as X-ray tube characteristic values for limiting the change amount of the rotor rotation period. The transmission timings of the respective data may be the same or different.

After step S1, the X-ray controller 29 determines whether a value approximately equal to an integer multiple of the X-ray intensity switching period coincides with the rotor rotation period (step S2). In step S2, the X-ray controller 29 compares an integer multiple of the X-ray intensity switching period with the rotor rotation period. The integer multiple corresponds to all natural numbers of 1 or more. At this time, it is not necessary to determine whether the rotor rotation period strictly coincides with an integer multiple of the X-ray intensity switching period. For example, it may be determined whether the rotor rotation period belongs to a predetermined numerical value range including an integer multiple of the X-ray intensity switching period. The predetermined numerical value range is, e.g., a range of ±0.01 msec with respect to an integer multiple of the X-ray intensity switching period. If the rotor rotation period falls within this predetermined numerical value range, the X-ray controller 29 determines that an integer multiple of the X-ray intensity switching period coincides with the rotor rotation period. If the rotor rotation period does not fall within this predetermined numerical value range, the X-ray controller 29 determines that a value approximately equal to an integer multiple of the X-ray intensity switching period does not coincide with the rotor rotation period.

If the X-ray controller 29 determines that a value approximately equal to an integer multiple of the X-ray intensity switching period does not coincide with the rotor rotation period (step S2: NO), it sets, as set values, the X-ray intensity switching period and rotor rotation period received in step S1.

Figure 6:
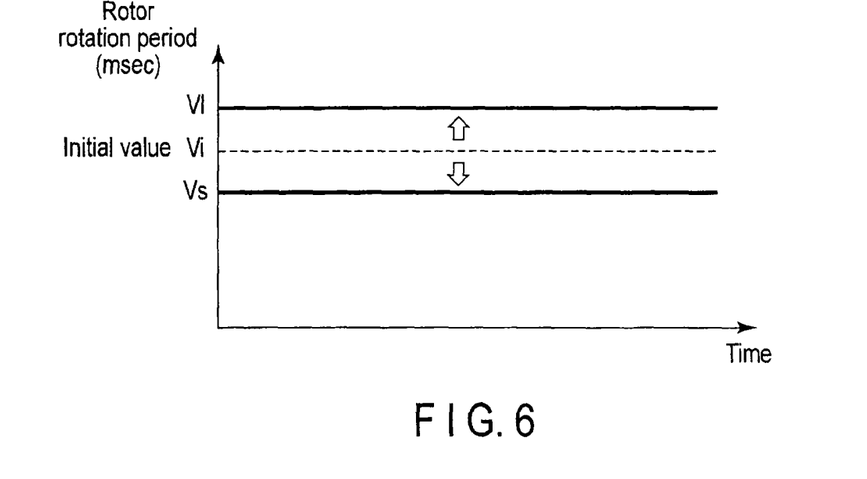
FIG. 6 is a chart for explaining a rotor rotation period change method by the X-ray controller in FIG. 2.

If the X-ray controller 29 determines that a value approximately equal to an integer multiple of the X-ray intensity switching period coincides with the rotor rotation period (step S2: YES), it changes the rotor rotation period (step S3). The rotor rotation period is changed to, e.g., a fixed value which does not coincide with an integer multiple of the X-ray intensity switching period. For example, as shown in FIG. 6, the rotor rotation period is set to a value shifted by about several Hz to 10 Hz from an initial value Vi of the rotor rotation period. The rotor rotation period is set to a value falling within a limited range based on X-ray tube characteristic values. Examples of the X-ray tube characteristic values are an X-ray output rating, rotor resonance period, and rotor critical speed. The X-ray output rating is defined as a combination of a maximum tube voltage value and maximum tube current value which can be loaded on the X-ray tube device 13. The minimum value of the rotor rotation period is defined by the combination of the maximum tube voltage value and maximum tube current value. The rotor rotation period is limited to a value which does not become smaller than the minimum value. The rotor resonance period is a rotor rotation period in which the vibration of the rotor 135 itself or anode 134 intensifies in resonance with rotation of the rotor 135. The rotor rotation period is limited to a value excluding this rotor resonance period. The rotor critical speed is a maximum speed at which the rotor 135 can rotate. A rotation period corresponding to this maximum speed corresponds to the maximum value of the rotor rotation period. The rotor rotation period is limited to a value which does not become larger than a rotation period corresponding to the rotor critical speed. The rotor rotation period may be set to a value V1 larger than or a value Vs smaller than the initial value Vi of the rotor rotation period, i.e., an integer multiple of the X-ray intensity switching period as long as the rotor rotation period is not an integer multiple of the X-ray intensity switching period and falls within the limited range based on the X-ray tube characteristic values.

Note that the X-ray tube characteristic values are not limited to the X-ray output rating, rotor resonance period, and rotor critical speed. In the embodiment, the limited range may be determined in consideration of any X-ray characteristic values capable of limiting the rotor rotation period, other than the X-ray output rating, rotor resonance period, and rotor critical speed.

If it is determined that an integer multiple of the X-ray intensity switching period does not coincide with the rotor rotation period (step S2: NO), or step S3 is executed, the X-ray controller 29 executes X-ray CT tomography while rotating the rotor 135 in the rotor rotation period set via step S2: NO or step S3 (step S4). In step S4, the X-ray controller 29 supplies, to the bias voltage generator 25, a control signal complying with the X-ray intensity switching period set by the user. The bias voltage generator 25 alternately switches the value of a bias voltage to be applied to the bias electrode in an X-ray intensity switching period corresponding to the supplied control signal. As a result, emission and cutoff of X-rays are alternately repeated in accordance with the X-ray intensity switching period.

Parallel to the control of the bias voltage generator 25, the X-ray controller 29 supplies, to the rotor control power generator 27, a control signal complying with the set vale of the rotor rotation period. The rotor control power generator 27 supplies, to the support mechanism 137, a driving signal pulse sequence complying with the supplied control signal. For example, a driving signal pulse sequence having a predetermined pulse repetition period corresponding to the changed rotor rotation period is supplied to the stator 136. The stator 136 rotates the rotor 135 in a rotor rotation period complying with the supplied driving signal pulse sequence. The rotor 135 rotates in a predetermined rotation period which is not an integer multiple of the X-ray intensity switching period and falls within the limited range based on the X-ray tube characteristic values. Since the rotor rotation period does not coincide with a value approximately equal to an integer multiple of the X-ray intensity switching period, thermoelectrons can uniformly collide with the electron beam orbital plane over a plurality of turns.

Figure 7:
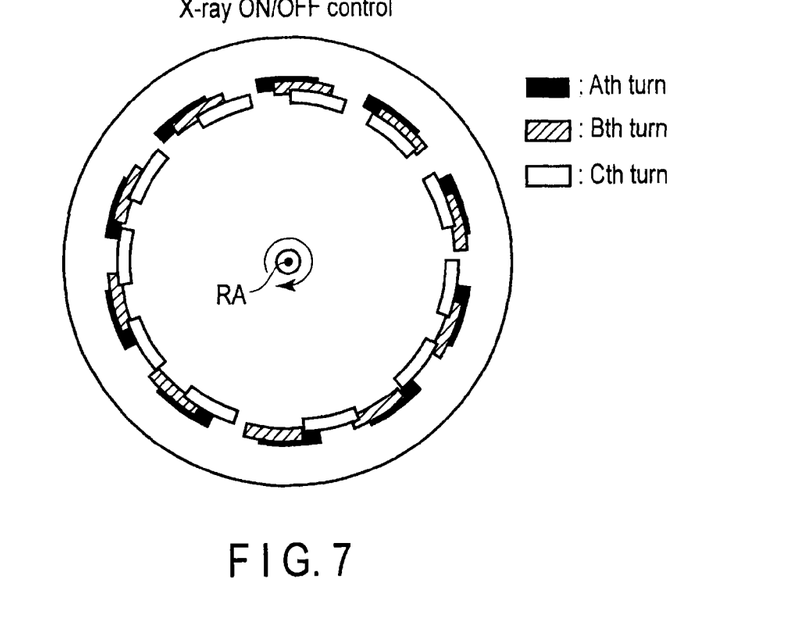
FIG. 7 is a view schematically showing scattering of thermoelectron collision surfaces on the anode when the X-ray controller in FIG. 2 changes the rotor rotation period.

FIG. 7 is a view schematically showing scattering of thermoelectron collision surfaces when the rotor rotation period is changed. As shown in FIG. 7, when the rotor rotation period does not coincide with a value approximately equal to an integer multiple of the X-ray intensity switching period, thermoelectrons do not limitedly collide with local portions on the anode 134 over a plurality of turns. For example, thermoelectron collision surfaces in the Ath turn, thermoelectron collision surfaces in the Bth turn, and thermoelectron collision surfaces in the Cth turn shift from each other on the electron beam orbital plane. In this fashion, by changing the rotor rotation period to fall within a numerical value range not coincident with a value approximately equal to an integer multiple of the X-ray intensity switching period, damage to the anode by thermoelectron collision can be uniformly distributed on the electron beam orbital plane. In FIG. 7, the radial positions of the thermoelectron collision surfaces in the Ath turn, the thermoelectron collision surfaces in the Bth turn, and the thermoelectron collision surfaces in the Cth turn shift from each other for illustrative convenience. However, these radial positions are the same in practice.

Figure 8:
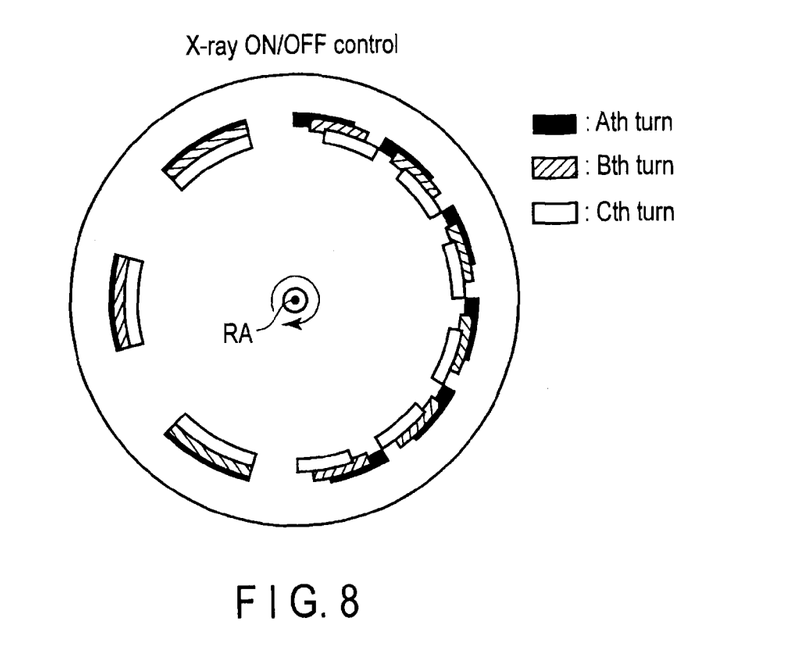
FIG. 8 is a view schematically showing another example of scattering of thermoelectron collision surfaces on the anode when the X-ray controller in FIG. 2 changes the rotor rotation period.

In FIG. 7, all thermoelectron collision surfaces on the anode 134 shift in the circumferential direction in every turn. However, the embodiment is not limited to this as long as damage to the anode can be reduced, compared to a case in which all thermoelectron collision surfaces on the anode 134 completely coincide with each other in the circumferential direction. Only some thermoelectron collision surfaces on the anode 134 may shift in the circumferential direction in every turn, as shown in FIG. 8. That is, some of thermoelectron collision surfaces formed on the anode 134 may be formed at the same local portions through a plurality of turns. In FIG. 8, similar to FIG. 7, the radial positions of the thermoelectron collision surfaces in the Ath turn, the thermoelectron collision surfaces in the Bth turn, and the thermoelectron collision surfaces in the Cth turn shift from each other for illustrative convenience. However, these radial positions are the same in practice.

An example of the rotor rotation period change processing has been described.

Note that the rotor rotation period change method is not limited to only a method of changing the rotor rotation period to a fixed value which is not an integer multiple of the X-ray intensity switching period and falls within the limited range based on the X-ray tube characteristic values.

Figure 9:
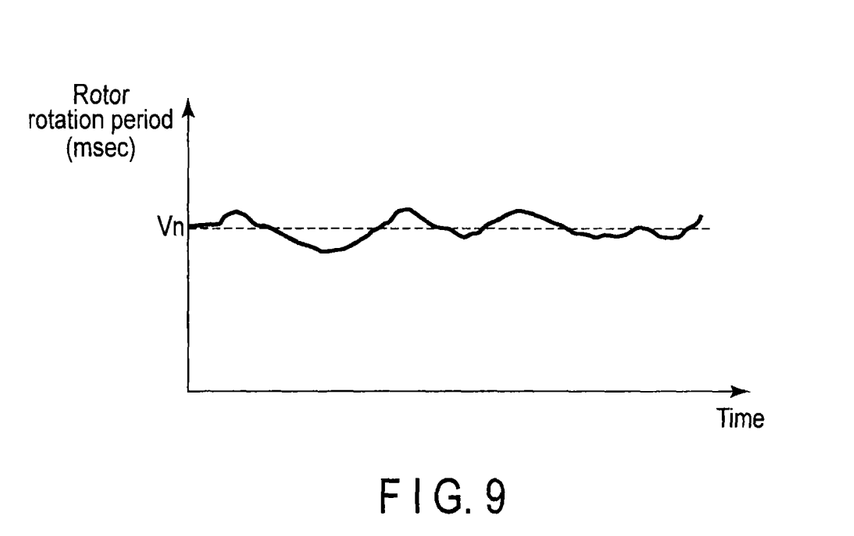
FIG. 9 is a chart for explaining another rotor rotation period change method by the X-ray controller in FIG. 2.

FIG. 9 is a chart for explaining another rotor rotation period change method. As shown in FIG. 9, in the second change method, the X-ray controller 29 fluctuates the rotor rotation period within a predetermined frequency range with respect to a reference value Vn. The predetermined frequency range is limited to the limited range based on the above-described X-ray tube characteristic values. The predetermined frequency range is desirably, e.g., about several Hz. The reference value Vn is preferably, e.g., the initial value Vi. However, the reference value Vn is not limited to the initial value Vi and is arbitrary as long as the value falls within the limited range based on the X-ray tube characteristic values. As shown in FIG. 9, the rotor rotation period may vary continuously along the time axis with respect to the reference value Vn, or vary intermittently in every reference time. The reference time may be, e.g., a time range set by a user, the X-ray intensity switching time, or the rotor rotation period.

When the second change method is adopted, the X-ray controller 29 applies the aforementioned fluctuation to the pulse repetition period of a driving signal pulse sequence supplied to the stator 136. Then, the rotor 135 rotates at a rotational frequency which varies in a predetermined value range with respect to an initial value or the like. In this case, the rotor rotation period varies, so thermoelectrons can uniformly collide with the anode 134 on the electron beam orbital plane. Therefore, damage to the anode 134 by thermoelectron collision can be uniformly distributed on the electron beam orbital plane.

Unlike the first change method, the second change method can easily deviate the rotor rotation period from the X-ray intensity switching period without searching for a value which is not an integer multiple of the X-ray intensity switching period and falls within the limited range based on the X-ray tube characteristic values. In the first change method, rotation control of the rotor 135 is simpler than in the second change method because the rotor rotation period is constant. When, therefore, the rotor rotation period can be set to a fixed value which is not an integer multiple of the X-ray intensity switching period and falls within the limited range based on the X-ray tube characteristic values, it is desirable to employ the first change method preferentially to the second change method. If the rotor rotation period cannot be set to a fixed value which is not an integer multiple of the X-ray intensity switching period and falls within the limited range based on the X-ray tube characteristic values, the second change method can be adopted. Note that the user may set the first change mode or second change method as the rotor rotation period change mode via the operation unit 47.

In the above description, X-ray modulation control is the tube current modulation method of switching the bias voltage to the bias electrode 133. However, the X-ray modulation control in the embodiment may be the tube voltage modulation method, as described above. In tube voltage modulation control, the X-ray controller 29 controls the high voltage generator 23 to alternately switch between the first tube voltage value and the second tube voltage value in accordance with a predetermined switching period. The high voltage generator 23 alternately applies, across the cathode 132 and the anode 134, a high voltage corresponding to the first tube voltage value and a high voltage corresponding to the second tube voltage value in synchronism with the switching period. As a method of quickly switching the tube voltage, there is known fast-kVp in which the tube voltage is switched between the first tube voltage value and the second tube voltage value for each view. In fast-kVp, the X-ray controller 29 controls the high voltage generator 23 to, for example, switch between a high voltage corresponding to a low tube voltage value and a high voltage corresponding to a high tube voltage value for each view. The low tube voltage value and high tube voltage value are arbitrary and can be, e.g., a combination of 80 kVp and 140 kVp suitable for Dual-Energy scan.

Modification

In the above description, the radiological image diagnostic apparatus is an X-ray computed tomography apparatus. A radiological image diagnostic apparatus according to a modification is assumed to be an X-ray diagnostic apparatus. The X-ray diagnostic apparatus according to the modification will be explained below. In the following description, the same reference numerals as those in the embodiment denote building elements having almost the same functions, and only if necessary, these building elements will be repetitively explained.

Figure 10:
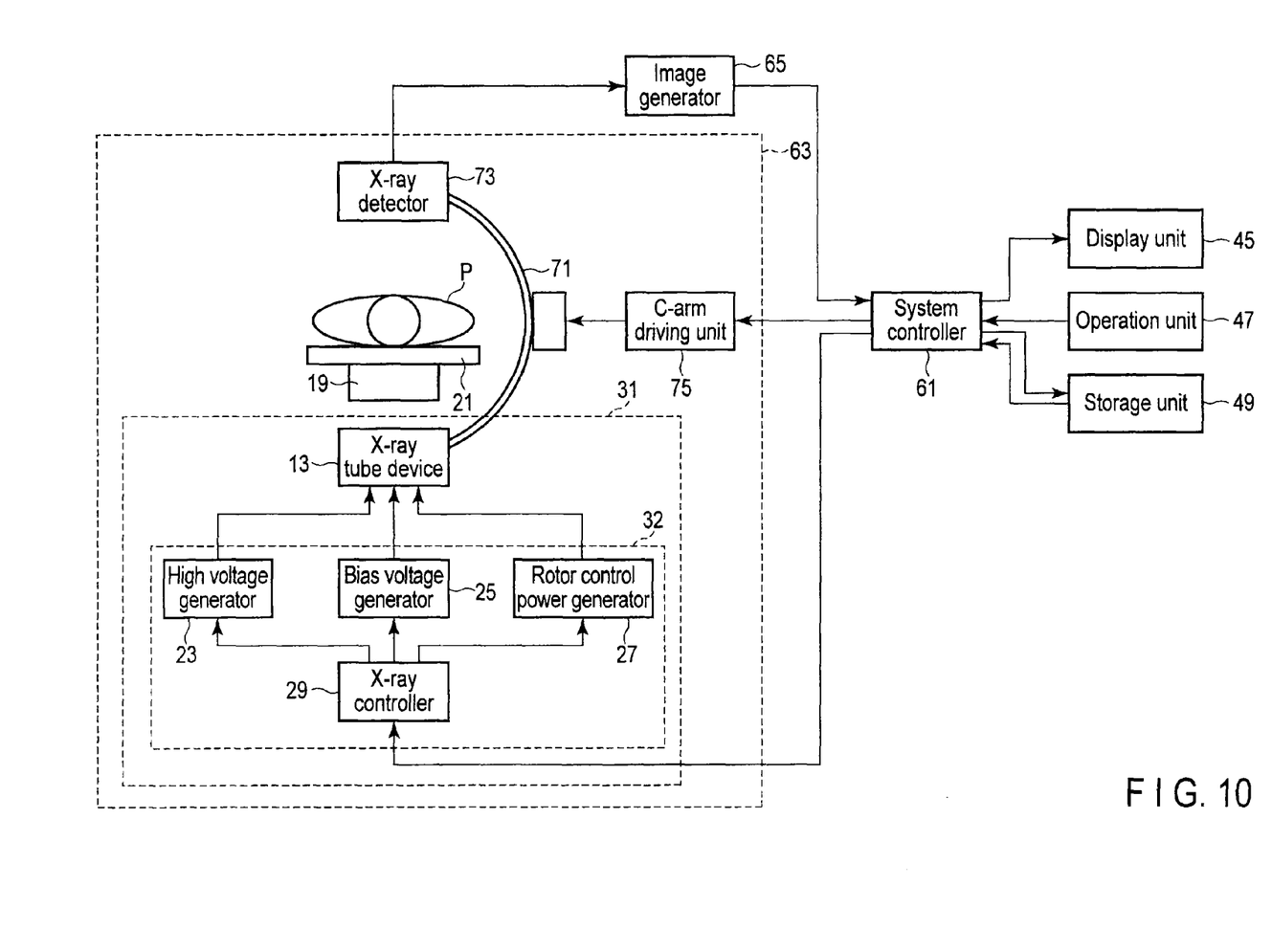
FIG. 10 is a view showing the arrangement of an X-ray diagnostic apparatus according to a modification of the embodiment.

FIG. 10 is a view showing the arrangement of the X-ray diagnostic apparatus according to the modification. As shown in FIG. 10, the X-ray diagnostic apparatus according to the modification includes a system controller 61 serving as a control center, an imaging mechanism 63, an image generator 65, the display unit 45, the operation unit 47, and the storage unit 49.

The imaging mechanism 63 includes a C-arm 71. The C-arm 71 is equipped with the X-ray tube device 13 and an X-ray detector 73 which face each other. The C-arm 71 pivotally supports the X-ray tube device 13 and X-ray detector 73. A C-arm driving unit 75 drives to pivot the C-arm 71. The C-arm driving unit 75 drives to pivot the C-arm in accordance with a control signal from the system controller 61.

The X-ray tube device 13 is connected to the high voltage generation device 32. The X-ray tube device 13 and high voltage generation device 32 constitute the X-ray generation device 31. The arrangement of the X-ray generation device 31 is almost the same as that of the X-ray generation device 31 mounted in the above-described X-ray computed tomography apparatus, and a description thereof will not be repeated.

The X-ray detector 73 detects X-rays generated by the X-ray tube device 13. For example, the X-ray detector 73 is implemented by a flat panel display (FPD). The X-ray detector 73 includes a plurality of detection elements arrayed two-dimensionally. Each detection element detects X-rays generated by the X-ray tube device 13, and generates an electrical signal corresponding to the intensity of the detected X-rays. The generated electrical signal is supplied to the image generator 65.

The image generator 65 generates an X-ray image of the subject P based on an electrical signal from the X-ray detector 73. The generated X-ray image data is supplied to the display unit 45 via the system controller 61.

The X-ray diagnostic apparatus according to the embodiment includes the X-ray controller 29, as described above. As described above, when a multiple of the X-ray intensity switching period coincides with the rotor rotation period, the X-ray controller 29 can change the rotor rotation period to uniformly distribute damage to the anode 134 by thermoelectron collision on the electron beam orbital plane.

As described above, the radiological image diagnostic apparatus according to the embodiment includes the cathode 132, anode 134, support mechanism 137, rotor control power generator 27, switching units 23 and 25, and X-ray controller 29. The cathode 132 generates thermoelectrons. The anode 134 generates X-rays upon receiving the thermoelectrons generated by the cathode 132. The support mechanism 137 supports the anode 134 to be rotatable about the rotation axis RA. The rotor control power generator 27 supplies power to the support mechanism 137. The switching units 23 and 25 are configured to switch the intensity of X-rays to be generated by the anode 134. The X-ray controller 29 controls the switching units 23 and 25 to switch the intensity of X-rays to be generated by the anode 134, and controls the rotor control power generator 27 to rotate the anode 134. At this time, when a value approximately equal to an integer multiple of an X-ray intensity switching period designated by a user coincides with the rotor rotation period, the X-ray controller 29 controls the rotor control power generator 27 to shift at least some thermoelectron collision ranges of the anode 134 in the first turn from thermoelectron collision ranges in the second turn.

With this arrangement, the X-ray computed tomography apparatus according to the embodiment can make thermoelectrons uniformly collide on the electron beam orbital plane when the anode 134 rotates a plurality of turns.

Accordingly, the embodiment can provide an X-ray computed tomography apparatus, high voltage generation device, and radiological image diagnostic apparatus capable of reducing partial damage to an anode. Further, the embodiment can suppress anode roughening arising from partial damage, discharge, and generation of nonuniformity of a dose.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X ray computed tomography apparatus, comprising:
an X-ray tube device including a cathode configured to generate a thermoelectron, an anode configured to generate an X-ray upon receiving the thermoelectron generated by the cathode, and a support mechanism configured to support the anode to be rotatable about a rotation axis;
an X-ray detector configured to detect the X-ray generated by the X-ray tube device;
a rotating frame configured to support the X-ray tube device to be rotatable about a subject;
a power generator configured to supply power to the support mechanism;
voltage generators configured to switch, by high-speed X-ray ON/OFF control and high-speed X-ray modulation, an intensity of an X-ray to be generated by the anode; and
a control circuit configured to control the voltage generators to switch the intensity of the X-ray to be generated by the anode, and control the power generator to rotate the anode, and when a value substantially equal to an integer multiple of a switching period of the intensity of the X-ray coincides with a rotation period of the anode, the control circuit is configured to control the power generator to shift at least some thermoelectron collision ranges of the anode in a first turn of the anode from thermoelectron collision ranges in a second turn of the anode.

2. The X-ray computed tomography apparatus according to claim 1, wherein the control circuit changes the rotation period to shift a thermoelectron collision range of the anode in the first turn from a thermoelectron collision range in the second turn.

3. The X-ray computed tomography apparatus according to claim 2, wherein the control circuit fixes the rotation period to a numerical value within a numerical value range not belonging to an integer multiple of the switching period.

4. The X-ray computed tomography apparatus according to claim 2, wherein the control circuit fluctuates the rotation period.

5. The X-ray computed tomography apparatus according to claim 1, further comprising a bias electrode placed between the cathode and the anode,
wherein one of the voltage generators applies a bias voltage between the bias electrode and the cathode.

6. The X-ray computed tomography apparatus according to claim 5, wherein
the control circuit controls the voltage generators to alternately switch the intensity of the X-ray between a first intensity and a second intensity higher than the first intensity, and
the first intensity is substantially zero.

7. The X-ray computed tomography apparatus according to claim 5, wherein the control circuit controls the voltage generators to alternately switch the intensity of the X-ray between a first intensity and a second intensity higher than the first intensity, and the first intensity is higher than zero.

8. The X-ray computed tomography apparatus according to claim 7, wherein one of the voltage generators applies a high voltage across the cathode and the anode.

9. The X-ray computed tomography apparatus according to claim 7, wherein the first intensity is a first tube voltage and the second intensity is a second tube voltage higher than the first tube voltage, and the control circuit controls the voltage generators to switch a tube voltage of the X-ray between the first tube voltage and the second tube voltage for each view.

10. The X-ray computed tomography apparatus of claim 1, wherein the control circuit is further configured to shift at least angular ranges of the thermoelectron collisions of the anode in the first turn of the anode from angular ranges of the thermoelectron collisions in the second turn of the anode, when the value substantially equal to the integer multiple of the switching period of the intensity of the X-ray coincides with the rotation period of the anode.

11. The X-ray computed tomography apparatus of claim 1, wherein a switching period of the intensity of the X-ray generated by the anode is shorter than the rotation period of the anode.

12. A high voltage generation device connected to an X-ray tube device including a cathode configured to generate a thermoelectron, an anode configured to generate an X-ray upon receiving the thermoelectron generated by the cathode, and a support mechanism configured to support the anode to be rotatable about a rotation axis, comprising:

a power generator configured to supply power to the support mechanism;

voltage generators configured to switch, by high-speed X-ray ON/OFF control and high-speed X-ray modulation, an intensity of an X-ray to be generated by the anode; and a control circuit configured to control the voltage generators to switch the intensity of the X-ray to be generated by the anode, and control the power generator to rotate the anode, and when a value substantially equal to an integer multiple of a switching period of the intensity of the X-ray coincides with a rotation period of the anode, the control circuit is configured to control the power generator to shift at least some thermoelectron collision ranges of the anode in a first turn of the anode from thermoelectron collision ranges in a second turn of the anode.

13. A radiological image diagnostic apparatus, comprising:

a cathode configured to generate a thermoelectron;

an anode configured to generate an X-ray upon receiving the thermoelectron generated by the cathode;

a support mechanism configured to support the anode to be rotatable about a rotation axis;

a power generator configured to supply power to the support mechanism;

voltage generators configured to switch, by high-speed X-ray ON/OFF control and high-speed X-ray modulation, an intensity of an X-ray to be generated by the anode; and a control circuit configured to control the voltage generators to switch the intensity of the X-ray to be generated by the anode, and control the power generator to rotate the anode, and when a value substantially equal to an integer multiple of a switching period of the intensity of the X-ray coincides with a rotation period of the anode, the control circuit is configured to control the power generator to shift at least some thermoelectron collision ranges of the anode in a first turn of the anode from thermoelectron collision ranges in a second turn of the anode.

* * * * *